United States Patent [19]
Yeh et al.

[11] Patent Number: 5,869,103
[45] Date of Patent: Feb. 9, 1999

[54] POLYMER MICROPARTICLES FOR DRUG DELIVERY

[75] Inventors: Ming-Kung Yeh, Taipei, Taiwan; Alan Gerald Coombes, Nottingham, United Kingdom; Paul George Jenkins, Macclesfield, United Kingdom; Stanley Stewart Davis, Nottingham, United Kingdom

[73] Assignee: Danbiosyst UK Limited, Nottingham, United Kingdom

[21] Appl. No.: 750,738

[22] PCT Filed: Jun. 19, 1995

[86] PCT No.: PCT/GB95/01426

§ 371 Date: Apr. 4, 1997

§ 102(e) Date: Apr. 4, 1997

[87] PCT Pub. No.: WO95/35097

PCT Pub. Date: Dec. 28, 1995

[30] Foreign Application Priority Data

Jun. 18, 1994 [GB] United Kingdom .................... 9412273

[51] Int. Cl.$^6$ ................................ A61K 9/50; B01J 13/02
[52] U.S. Cl. ........................... 424/501; 424/502; 264/4.1; 264/4.6
[58] Field of Search .................................... 424/501, 502; 264/4.1, 4.6

[56] References Cited

U.S. PATENT DOCUMENTS

| 4,526,938 | 7/1985 | Churchill et al. ........................ 424/499 |
| 5,543,158 | 8/1996 | Gref ........................................ 424/501 |

FOREIGN PATENT DOCUMENTS

| 0 486 959 B1 | 5/1992 | European Pat. Off. . |
| 3 916 020 A1 | 11/1990 | Germany . |

OTHER PUBLICATIONS

Jani, et al., "The Uptake and Translocation of Latex Nanospheres and Microspheres after Oral Administration to Rats," *J. Pharm. Pharmacol.* 41(12):809–812 (1989).

Jeffery, et al., "The preparation and characterisation of poly(lactide–co–glycolide) microparticles. I: Oil–In–water emulsion solvent evaporation," *Int. J. Pharm.* 77(2–3):169–175 (1991).

Jeffery, et al., "The Preparation and Characterization of Poly(lactide–co–glycolide) Microparticles. II. The Entrapment of a Model Protein using a (Water–in–Oil)–in–Water Emulsion Solvent Evaporation Technique," *Pharm. Res.* 10(3):362–368 (1993).

Jenkins, et al., "The quantitation of the absorption of microparticles into the intestinal lymph of Wistar rats," *Int. J. Pharm.* 102(1–3):261–266 (1994).

Kwong, et al., "In vitro and In Vivo Release of Insulin from Poly(lactic Acid) Microbeads and Pellets," *J. Control Release* 4(1):47–62 (1986).

Leelarasamee, et al., "A method for the preparation of polylactic acid microcapsules of controlled particle size and drug loading," *J. Microencapsulation* 5(2):147–157 (1988).

(List continued on next page.)

*Primary Examiner*—Carlos A. Azpuru
*Attorney, Agent, or Firm*—Arnall Golden & Gregory, LLP

[57] ABSTRACT

Provided are biodegradable microparticles, which exhibit a linear release profile of active agent, and methods for making the microparticles. The microparticles include a mixture of a biodegradable polymer, a water soluble polymer, and an active agent. Preferred biodegradable polymers include lactide homopolymers or copolymers of lactide and glycolide, and preferred water soluble polymers include poly(ethylene glycol) (PEG) or PEG copolymers. The microparticles are made using an emulsion/solvent extraction method, in which the continuous phase of the secondary emulsion contains an organic solvent that is miscible with the organic solvent in the primary emulsion.

26 Claims, 3 Drawing Sheets

OTHER PUBLICATIONS

Ogawa, et al., "A New Technique to Efficiently Entrap Leuprolide Acetate into Microcapsules of Polylactic Acid or Copoly(Lactic/Glycolic) Acid," *Chem. Pharm. Bull.* 36(3):1095–1103 (1988).

Raghuvanshi, et al., "Biodegradable delivery system for single step immunization with tetanus toxoid," *Int. J. Pharm.* 93(1–3):R1–R5 (1993).

Singh, et al., "Controlled Delivery of Diphtheria Toxoid Using Bioerodable Poly(D,L–Lactide) Microcapsules," *Pharm. Res.* 8(7):958–961 (1991).

Singh, et al. "Immunogenicity studies on diphtheria toxoid loaded biodegradable microspheres," *Int. J. Pharm.* 85(1–3):R5–R8 (1992).

Smith, et al., "Measurement of Protein Using Bicinchoninic Acid," *Anal. Biochem.* 150(1):76–85 (1985).

Visscher, et al., "Effect of particle size on the in vitro and in vivo degradation rates of poly(DL–lactide–co–glycolide) microcapsules," *J. Biomedical Material Res.* 22(8):733–746 (1988).

Wada, et al., "In Vitro Evaluation of Sustained Drug Release from Biodegradable Elastomer," *Pharm. Res.* 8(10):1291–1296 (1991).

Wang, et al., "Influence of formulation methods on the in vitro controlled release of protein from poly(ester) microspheres," *J. Cont. Rel.* 17(1):23–32 (1991).

Watts, et al., "Microencapsulation Using Emulsification/ Solvent Evaporation: An Overview of Techniques and Applications," *Crit. Rev. Ther. Drug Carrier Syst.* 7(3):235–259 (1990).

Alonso, et al., "Determinants of Release Rate of Tetanus Vaccine from Polyester Microspheres," *Pharm. Res.* 10(7):945–953 (1993).

Benita, et al., "Characterization of Drug–Loaded Poly(d, l–lactide) Microspheres," *J. Pharm. Sci.* 73(12):1721–1724 (1984).

Bodmeier, et al., "The Preparation and Evaluation of Drug– Containing Poly(dl–lactide) Microspheres Formed by the Solvent Evaporation Method," *Pharm. Res.* 4(6):465–471 (1987).

Cohen, et al., "Controlled Delivery Systems for Proteins Based on Poly(Lactic/Glycolic Acid) MIcrospheres," *Pharm. Res.* 8(6):713–720 (1991).

Eldridge, et al., "Biodegradable Microspheres: Vaccine Delivery System for Oral Immunization," *Curr. Top. Micro. Immunol.* 146:59–66 (1989).

Eldridge, et al., "Controlled Vaccine Release In The Gut–Associated Lymphoid Tissues. I. Orally Administered Biodegradable Microspheres Target The Peyer's Patches," *J. Cont. Rel.* 11(1—3):205–214 (1990).

Eldridge, et al., "Biodegradable and Biocompatible Poly- (DL–Lactide–Co–Glycolide) MIcrospheres as an Adjuvant for Staphylococcal Enterotoxin B Toxid Which Enhances the Level of Toxin–Neutralizing Antibodies," *Infec. Immun.* 59(9):2978–2983 (1991).

Florence, et al., "Controlled Release of Drug: Polymers and Aggregate Systems," pp. 163–184 (Morton Rosoff, VCH Publishers, N.Y. 1988).

Fong, et al., "Evaluation of Biodegradable Microspheres Prepared by a Solvent Evaporation Process Using Sodium Oleate as Emulsifier," *J. Cont. Rel.* 3:119–130 (1986).

Hora, et al., "Release of Human Serum Albumin from Poly(lactide–co–glycolide) Microspheres," *Pharm. Res.* 7(11):1190–1194 (1990).

Hunter, et al., "Adjuvant activity of non–ionic block copoly- mers. IV. Effect of molecular weight and formulation on titre and isotype of antibody," *Vaccine* 9(4):250–256 (1991).

POLYMER MICROPARTICLES FOR DRUG DELIVERY

RELATED APPLICATIONS

Priority is claimed under 35 U.S.C. § 119 to PCT/GB95/01426, filed Jun. 19, 1995, which corresponds to GB 94112273.6, filed Jun. 18, 1994.

FEDERALLY SPONSORED RESEARCH

Not applicable.

BACKGROUND OF THE INVENTION

1. Field of the Invention

The present invention relates to polymer microparticles for administering active agents, and to a method for making such particles.

2. Background Art

It is possible to deliver therapeutic agents in the form of drugs and vaccines to the body by a variety of routes that include parenteral and nonparenteral access. The products of biotechnology represent a special class of materials. Today the pharmaceutical scientist is faced with the problem of delivering therapeutically active materials in the form of peptides and proteins, carbohydrates, oliogonucleotides and DNA.

Considerable interest exists in the use of colloidal particles for the delivery of therapeutically active materials in the form of proteins and peptides and for vaccine formulation. Various biodegradable polymers have been investigated as therapeutic carriers, including serum albumin beads, polyacryl starch microparticles, polyacrylamide, microparticles, poly(butyl-2-cyanocrylate) nanoparticles and polylactide co-glycolide microparticles (Florence et al). In the case of albumin and polyacryl starch, antibody responses were induced to the carriers as well as to the specific antigens entrapped therein. Problems of toxicity associated with polyacrylamide and poly(butyl-2-cyanoacrylate) limit the use of these polymers as antigen delivery systems.

Microparticles based upon resorbable copolymers of polylactide and polyglycolide have been widely investigated for drug delivery (Watts, et al) and are now finding increasing application for the delivery of the products of biotechnology (especially peptides and proteins) (Kwong, et al and Wang, et al). These synthetic polyesters are approved for human use and have a 25 year history of safety. Injected poly(DL-lactide-co-glycolide) (PLG) microparticles exhibit good biocompatibility and induce only a minimal inflammatory response. The lactide copolymers such as PLG are good candidates for the development of controlled release drug systems and vaccines. They biodegrade through hydrolysis of ester linkages to yield the normal body constituents lactic acid and glycolic acid. The degradation rate of lactide copolymers is controlled by various factors including molecular weight, lactide: glycolide ratio and polymer crystallinity and can be varied from several weeks to over a year, thus potentially allowing control over the time and rate of vaccine release. Carriers may therefore be designed to release entrapped antigen at certain intervals after immunization when booster doses are normally administered.

A large number of microencapsulation techniques have been developed using PLG, such as film casting, moulding, spray drying and extrusion, but the most common is the solvent evaporation technique (Fong, et al., and Bodmeier et al.,). Although the oil-in water (O/W) emulsion/solvent evaporation technique has been used successfully by several groups to entrap hydrophobic substances such as progesterone, poor encapsulation efficiency results for moderately water-soluble and water soluble drugs due to partition into the aqueous continuous phase (Benita. et al.,). This presents a major problem in drug and vaccine delivery.

Protein encapsulation in PLG microparticles has been attempted previously using oil-in oil (O/O) and O/W techniques wherein dried protein is first dispersed in a solution of PLG (Alonso. et al). In the O/O technique, the dispersion may be emulsified in silicone oil containing SPAN 85™ as a stabiliser. The addition of petroleum ether subsequently results in solvent extraction and precipitation of the microparticles. Although protein loadings are close to the theoretical maximum, the particle size tends to be large ( around 500 $\mu$m ) and the particle shape irregular. Leelarasamee et al described a solvent partitioning method which involved slowly injecting a suspension of hydrocortisone in a PLA solution into a stream of mineral oil. In a related method, Wada et al encapsulated hydrophilic drugs in lactic acid oligomer microparticles using an acetonitrile/water mixture to form the primary emulsion. This was subsequently emulsified in cottonseed oil and the solvent was removed by heating.

In the O/W approach a suspension of protein in the polymer solution is emulsified with an immiscible aqueous surfactant solution which results in polymer precipitation and hardening of the microparticles. Solvent is removed by evaporation. Microparticles less than 10 $\mu$m in size may be produced but the protein is inefficiently encapsulated in the microparticles prepared in the presence of water, due to partition into the aqueous phase. Faster and less reproducible protein release has also been noted when the protein is dispersed as a lyophilised powder in the polymer solution (Alonso, et al).

In order to improve the loading of water soluble compounds within PLG microparticles Ogawa et al used a water-in oil-in water (W/O/W ) solvent evaporation technique to entrap a water soluble peptide into PLG microparticles. The W/O/W technique has since become one of the principle methods for encapsulating proteins and peptides (Jeffery, et al). In this double emulsion-solvent evaporation approach, an aqueous solution of the protein is emulsified with the polymer solution to form a primary water-in-oil emulsion (W/O). This is subsequently emulsified with an aqueous surfactant solution (W/O/W) to induce polymer precipitation and microparticle hardening and to allow solvent removal by evaporation. The W/O/W method has been used to encapsulate diphtheria toxoid in DL.PLA controlled release microparticles (Singh, et al.) and tetanus toxoid in PLA and DL.PLG respectively (Raghuvanshi, et al) with the aim of producing single dose vaccines which potentially overcome problems of patient noncompliance, vaccine administration and storage.

A recent publication has described the incorporation of ovalbumin in PLG particles using the W/OIW method (Uchida and Goto, Biol. Pharm. Bull. 17(1994) 1272–1276). The particles were in the size range 1 to 14 $\mu$m. The authors commented on the low loading efficiencies (8–20%). The content of ovalbumin in the microparticles was expected to be from 0.08 to 0.20%.

Microparticles which are administered subcutaneously either remain in the subcutaneous tissue or are phagocytosed depending on their size (Visscher, et al). The encapsulation of antigens in microparticles less than 10 $\mu$m is of interest for targeting to macrophages (Eldridge, et al). Several studies (Eldridge, et al., and Jenkins, et al., and Jani, et al.) have shown that there is also a significant dependency on size for the absorption of microparticles across the gastrointestinal tract after oral delivery, with microparticles of 0.5–1.0 μm being absorbed in the greatest numbers. Thus, the ability to easily control the particle size is desirable.

SUMMARY OF THE INVENTION

It has surprisingly been found that microparticles comprising a mixture of a biodegradable polymer and a water soluble polymer achieve a greatly improved loading of active agent and can give a linear release time profile for the active agent. Furthermore, it has been found that preparation of polymer microparticles using an emulsification/solvent extraction method in which miscible organic solvents are used significantly reduces partitioning of the active agent into the continuous phase of the secondary emulsion, especially when the active agent is water-soluble.

It is therefore an object of the present invention to provide microparticles that include a mixture of a biodegradable polymer and a water soluble polymer, and an active agent.

DETAILED DESCRIPTION OF THE INVENTION

Figure 1:
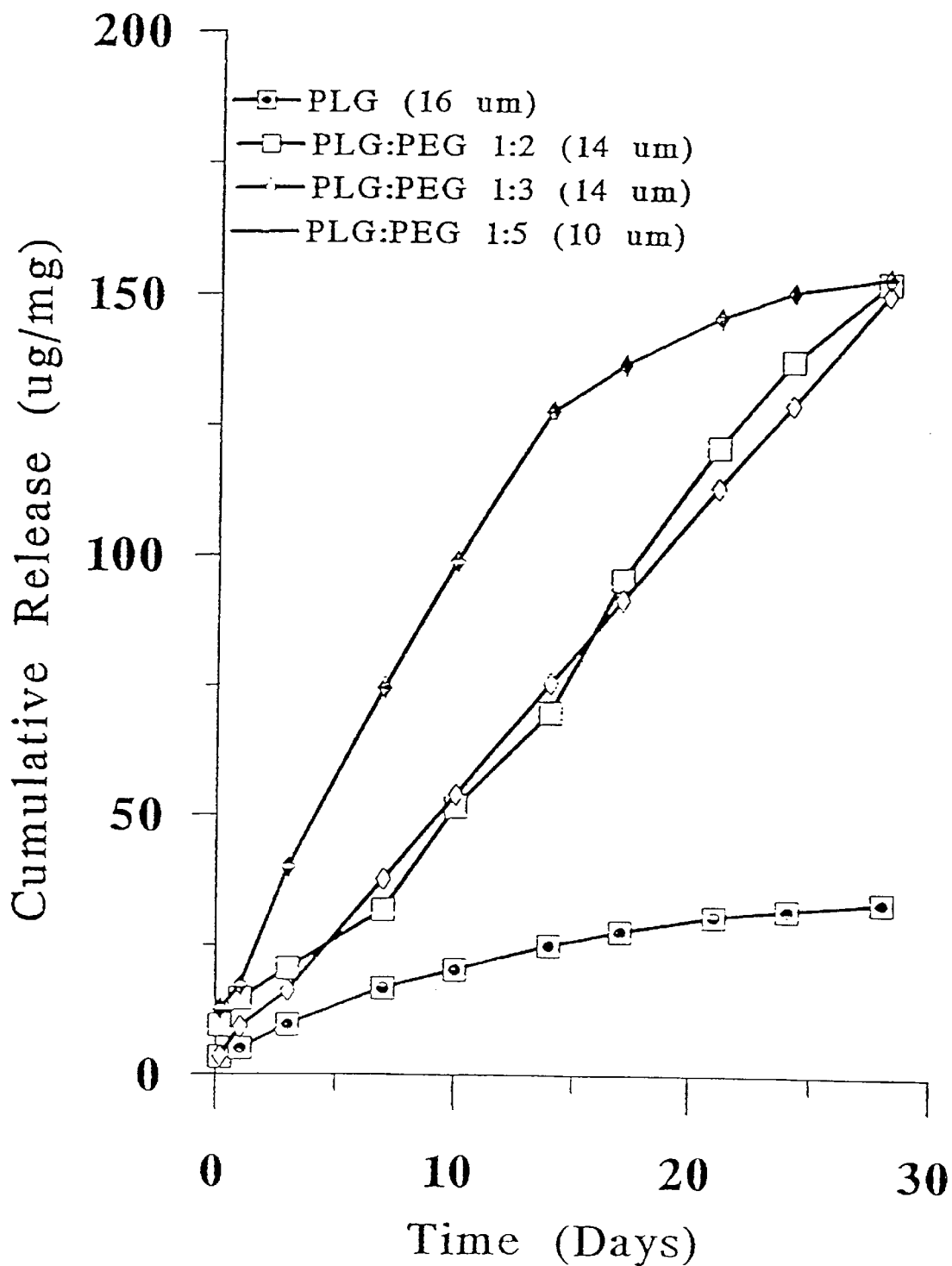
FIG. 1 is a graph showing the cumulative release profiles of OVA from PLG microparticles prepared using PLG:PEG solution.
Figure 2:
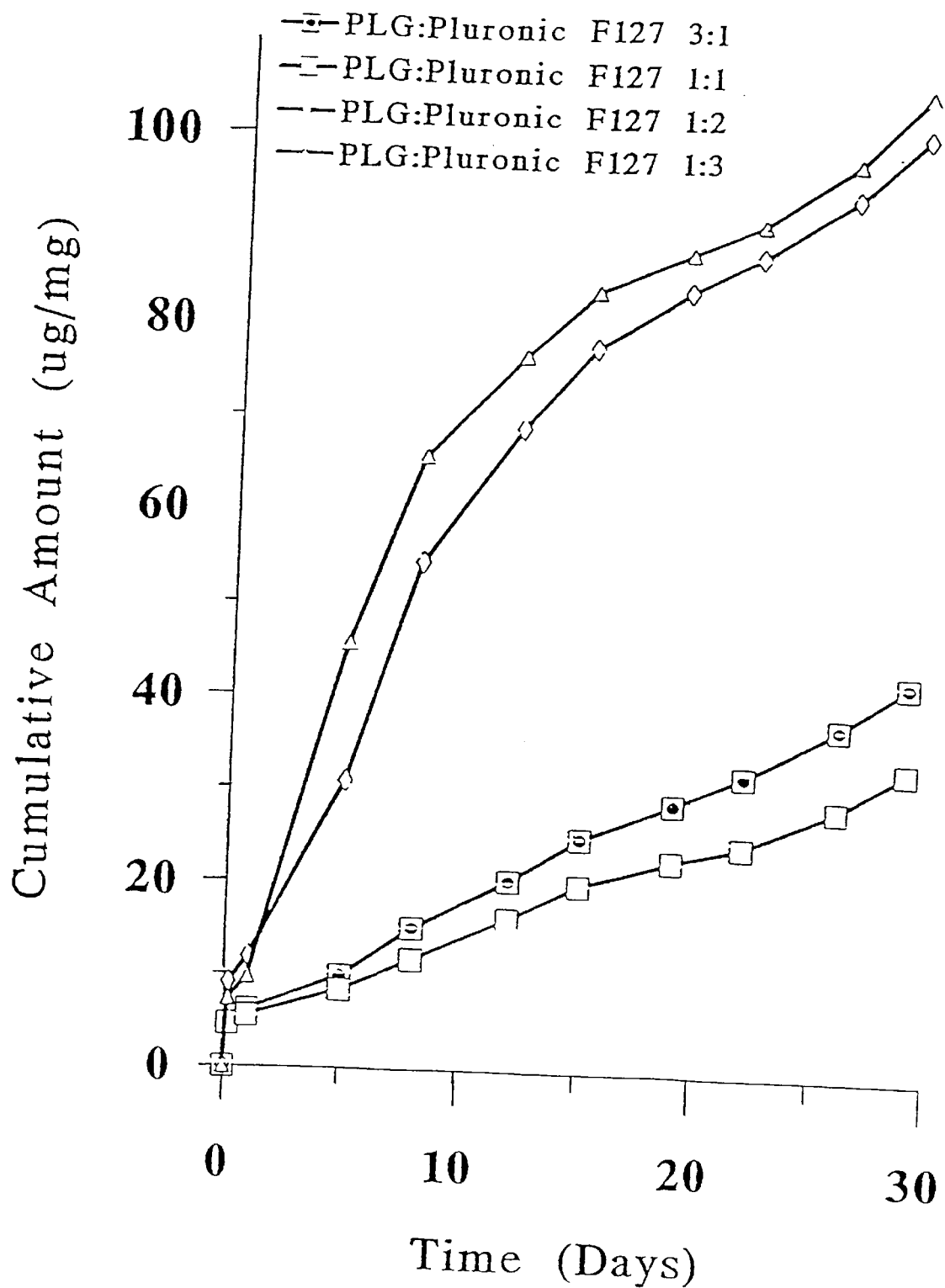
FIG. 2 is a graph showing the cumulative release profiles of OVA from PLG microparticles prepared using PLG:Pluronic solution.

The term microparticle is used herein to include nanoparticles. The microparticles preferably have a size in the range 10 nm to 200μm. The water-soluble polymer is preferably soluble in both water and dichloromethane (DCM).

The term "biodegradable polymer" is used herein to include polymeric systems which can degrade into low molecular weight compounds which are known to be involved normally in metabolic pathways. The term also includes polymer systems which can be attached in the biological milieu so that the integrity of the system, and in some cases of the macromolecules themselves, is affected and gives fragments or other degradation by-products which can move away from their site of action, but not necessarily from the body.

The ratio of biodegradable polymer to water-soluble polymer is in the range 99.9:1.0 to 10:90, more preferably 90:10 to 10:90.

Suitable biodegradable polymers for producing the microparticles are polyesters such as polylactide, polyglycolide, copolymers of lactide and glycolide, polyhydroxybutyrate, polycaprolactone, copolymers of lactic acid and lactone, copolymers of lactic acid and PEG, copolymers of a-hydroxy acids and α-amino acids (polydepsipeptides), polyanhydrides, polyorthoesters, polyphosphazenes, copolymers of hydroxybutyrate and hydroxyvalerate, poly (ethylene carbonate), copoly(ethylene carbonate). polyethylene terephthalate or mixtures of these polymers.

The preferred resorbable/biodegradable polymers are lactide homopolymers poly(L-lactide), poly(D,L-lactide), and copolymers of lactide and glycolide such as 50:50 poly(DL lactide co-glycolide)(PLG). The PLG preferably has a molecular weight in the range 5–100 kD.

While poly(ethylene glycol) (PEG) is the preferred water soluble polymer for mixing with the biodegradable polymer, other suitable water soluble polymers include poly (oxyethylene oxide)(PEO), poly(oxyethylene)-poly (oxypropylene) [PEO-PPO] block copolymers such as triblock PEO-PPO-PEO copolymers (POLOXAMERS™, PLURONICS™) and tetra-functional block copolymers derived from the sequential addition of propylene oxide and ethylene oxide to ethylene diamine (POLOXAMINES™, TETRONICS™), copolymers of PEG with poly(lactic acid), oligomers of poly(lactic acid), lactides, copolymers of PEG and amino acids, conjugates of PEG with polysaccharides for example a conjugate produced from 40000 MW dextran and polyoxyethylene-glycol monomethyl ether and others as described by Duval et al. in Carbohydrate Polymers, 15, (1991), 233–242, conjugates of PEG with proteins such as those described by Nucci et al., in Advances in Drug Delivery Review, 6, (1981), 113–151, or with collagen as described by Rhee et al in Poly(ethylene glycol) chemistry. Biotechnical and Biomedical Applications. Ed. J. Milton Harris, Plenum Press (1992) or conjugates of PEG with colony Stimulating Factor (CSF-1) as described by Katre N. V. in The conjugation of proteins with polyethylene glycol and other polymers. Adv. Drug Delivery Reviews, 10, 91–114 (1993). Conjugates of PEG with bioactive agents such as enzymes, vitamins, steroids and drugs such as 5-fluoro-uracil.

The molecular weight of PEG is in the range 100–100,000. The molecular weight of PEO is usefully in the range 100,000 to 500,000.

Further provided is a method of forming polymer microparticles containing an active agent, which includes the steps of:

a. forming an aqueous solution, water-in-oil (W/O) emulsion or a suspension of the active agent in a first organic solvent;

b. mixing the aqueous solution, W/O emulsion or suspension of the active agent with a polymer solution formed in a second organic solvent;

c. mixing the emulsion so formed in step b. with a continuous phase comprising a third organic solvent which is miscible with the first and second organic solvents and is not a solvent for the polymer.

The continuous phase causes precipitation of the polymer, extraction of the first and second solvents and hardens the microspheres.

The microparticles are then harvested, cleaned and stored according to usual methods.

The first and second organic solvents may be the same or different and are preferably selected from dichloromethane (DCM), chloroform, acetone, ethyl acetate, ethyl formate or mixtures thereof.

The dry active agent can be added directly to the solution of polymer in the second organic solvent. Thus the solvent used to prepare the water-in-oil emulsion or suspension of the active agent may already contain the dissolved polymer.

The third organic solvent is preferably a lower alcohol having 1 to 6 carbon atoms and is more preferably methanol or ethanol.

The first organic solvent preferably contains a stabiliser. Suitable stabilisers include Sorbitan esters, SPAN 60™ (Sorbitan monostearate), glyceryl monoesters, such as glyceryl monostearate, and nonyl phenol ethoxylates or any other stabiliser which is soluble in the first organic solvent. The continuous phase preferably contains a surfactant such as polyvinyl pyrrolidone (PVP) or any other surfactant which is soluble in the third organic solvent.

The emulsification/solvent evaporation technique for preparation of PLG microparticles is generally based on the use of immiscible liquids to form droplets of polymer solution in a continuous phase which subsequently harden to form microparticles by polymer precipitation and solvent removal. An exception is the nanoprecipitation method of Fessi et al. in which spherical particles may be produced by adding a solution of PLG in acetone to water.

In contrast however, the method disclosed herein makes use of miscible organic phases for example DCM and methanol, to form microparticles. This method has been found to result in significantly higher entrapment of active agent and greatly reduces the partitioning of the agent into the continuous phase.

The term "active agent" is used herein to include any agent which it may be desired to administer to the human or animal body for any purpose, including therapeutic, pharmaceutical, pharmacological, diagnostic, cosmetic and prophylactic agents. The term is also used to include any agents which it may be desired to administer to plants by controlled release, such as agrochemicals including herbicides, pesticides and fertilizers.

The active agent is preferably water-soluble. The term 'water-soluble' is used herein as referring to a material which is soluble in water to give a solution of at least 1 mg/ml.

The active agent is preferably a polypeptide, peptide or protein, a carbohydrate or an oligonucleotide such as DNA.

Suitable active agents include growth hormone, insulin, interferons (alpha, beta, gamma), erythropoietin, colony stimulating factors, parathyroid hormone, leutenizing hormone releasing hormone, calcitonin, heparin, somatostatin and various analogues thereof.

The active agent may also be an antigen for use in vaccines and these include polypeptides, proteins, glycoproteins that are obtained from bacterial, viral and parasitic sources or produced by synthetic methods. The term 'antigen' is used herein to include any material which will cause an antibody reaction of any sort when administered. Such antigens can be administered by injection or to various mucosal sites (nasal, oral, vaginal, rectal, colonic).

Vaccines for the treatment of allergens and for auto immune diseases are well described in the prior art. For example in autoimmune disease it has been suggested that the slow administration of essential factors can be beneficial. Such factors can include insulin for the treatment of diabetes and collagen for treating rheumatoid arthritis.

The microparticles are useful for delivering a wide range of active agents and can be administered by a wide range of routes, depending on the agent to be delivered. The microparticles may be adapted for injection, either intramuscularly, intravenously, subcutaneously, intraarticularly or intraperitoneally. The microparticles may be adapted for administration to the dermal or epidermal layer of the skin by injection or needleless injector system. The microparticles may also be adapted for administration to mucosa such as the nose, the gastrointestinal tract the colon, vagina or rectum, or administered to the eye.

The microparticles preferably have a size in the range 10 nm to 200 $\mu$m. The size chosen for a particular microparticle will depend on the active agent to be delivered, and the intended route of administration.

For oral delivery, particles are conveniently in the size range 0.5 to 5.0 $\mu$m. For subcutaneous delivery, a suitable size is <100 $\mu$m. Microparticles for extravascular delivery to the spleen, liver and bone marrow preferably have a size of <100 nm.

Microparticles for parenteral delivery conveniently have a size of <200 $\mu$m, preferably <150 $\mu$m. Microparticles adapted for intra-arterial chemo-embolisation therapy are preferably of a size up to 100 $\mu$m and microparticles for targeting an agent to the lung capillaries conveniently have a size in the range of 7 $\mu$m.

The desired particle size can be obtained by varying the process parameters in manners well known to those skilled in the art. For example changing the particular polymer type used and its molecular weight will change the particle size, an increase in polymer molecular weight generally increasing the particle size. Increasing the polymer concentration also increases particle size.

The microparticles disclosed herein provide a controlled release system which is useful for delivery of a wide range of active agents. A particularly significant advantage has been found with the particles disclosed herein, namely that a linear or zero order release profile of the active agent can be achieved. Such a release profile is particularly advantageous for the controlled release of certain bioactive agents such as proteins.

In addition, the use of the mixture of biodegradable and water-soluble polymers in the microparticles disclosed herein has been found to allow a significant increase in the amount of active agent incorporated into the particles, whilst still giving a linear release profile. This combination of properties has not been achieved with prior art particles comprising only biodegradable polymers.

The protein content of prior art resorbable PLG microparticles produced by the conventional emulsification/ solvent evaporation (W/O/W) method can be increased by increasing the amount of protein in the primary emulsion. However, a significant "burst" release of protein occurs in the first 24 hours of release testing due to surface location of protein. In addition the release pattern is often non linear, being characterised by a rapid release phase, (the "burst effect", followed by a lag phase when little or no protein is released, followed by a steady rate of release (Cohen et al., in Pharmaceutical Research, 8, 1991, 713–720 (1991)). In other instances, the cumulative amount of protein released from resorbable microparticles shows a linear relationship with the square root of time, signifying a process controlled by diffusional release of protein through a network of water filled channels (Hora et al. in Pharmaceutical Research, 7, 1190–1194 (1990)).

The microparticles disclosed herein do not suffer from a significant burst release of active agent followed by a lag period when little or no release is seen. Instead, the microparticies disclosed herein have reduced this problem and are found to give a linear release of active agent.

In the preferred embodiment, since PEG is readily soluble in water, the resorption rate of PLG:PEG blended microparticles would be expected to be substantially modified relative to the unblended PLG system due to PEG leaching from the microparticles to leave a highly porous matrix. Fine control over protein release rate is feasible by appropriate changes in PEG characteristics and content.

The method disclosed herein has also been found to help in achieving an increased loading of active agent in the particles due to the third organic solvent used in the continuous phase. Additionally, the inclusion of a stabiliser such as SPAN 60™ in the first organic solvent has been found to contribute to the reduction of the "burst" effect found with the microparticles disclosed herein.

In a preferred embodiment, microparticles containing a mixture of PLG with PEG, made by a method using methanol as the third organic solvent, were found to achieve a significant increase in loading of the active protein agent and to exhibit a zero order release pattern of protein over 30 days during in vitro incubation at 37° C.

Preferred embodiments of the compositions and methods will be further understood from the following non-limiting examples.

Materials:

50:50 poly(DL-lactide-co-glycolide), (molecular weight 9000, RG503), 75:25 poly(DL-lactide-co-glycolide), (molecular weight 17,000, RG755), 85:15 poly(DL-lactide-co-glycolide), (molecular weight 54,000, RG858), poly(D,L-lactide):(PLC, molecular weight 332,000, R208), were supplied by Boehringer Ingelheim, Ingelheim, Germany. Polyvinyl alcohol (PVA) (13–23000, 87–89% hydrolyzed), and poly(vinyl pyrrolidone) (PVP) (MW 40,000 ) were obtained from Aldrich Chemical Co. Inc., Dorset. U.K. Dichloromethane (DCM), and methanol (HPLC grade) were supplied by Fisons, Loughborough, U.K. Ovalbumin (OVA) (grade V), Insulin, leutinising hormone releasing hormone (LHRH), polyethylene glycol (MW 8000) and Span 60 were obtained from Sigma Chemical Co., Dorset. U.K. Pluronic polyethylene oxide-polypropylene oxide block copolymers L44, L121, L122, L123 and F127 were obtained from BASF Co., Parsippany. N.J. U.S.A.. All materials were used as supplied.

The formulations described in the following examples were all prepared using the 50:50 PLG copolymer (RG 503) unless otherwise specified.

Example 1. Basic formulation of microparticles

A solution of Span 60 in DCM (2 ml, 0.5% w/v) was emulsified with an ovalbumin (OVA) aqueous solution (1 ml, 30 mg/ml) using a Silverson homogeniser (Silverson machines, Chesham Bucks U.K) to provide the primary emulsion. The emulsion was then mixed at high speed for 2 minutes with 5 ml polymer solution (6% w/v PLG in dichloromethane) and emulsified for 4 minutes with a continuous phase solution, methanol (20 ml), containing 10% w/v PVP as an emulsion stabilizer. The resulting W/O/O emulsion was stirred for 3–4 hours under ambient conditions to extract DCM. The microparticles were cleaned by centrifuging and resuspension in distilled water a total of three times and then freeze dried. The final product was stored in a desiccator below 4° C.

Example 2. The effect of concentration of Span in the primary emulsion

A solution of Span 60 in DCM (2 ml) ( 0.1 to 20.0% w/v) was emulsified with an OVA aqueous solution (1 ml, 30 mg/ml) using a Silverson homogeniser to provide a primary emulsion. The resulting emulsion was then emulsified at high speed with polymer solution (6% w/v PLG in DCM) and emulsified with a continuous phase solution, methanol, containing 10% w/v PVP as an emulsion stabilizer. The resulting w/o/o emulsion was stirred for 3–4 hours under ambient conditions to extract DCM. The microparticles were cleaned, freeze dried and stored as described above.

Determination of OVA Loading of Microparticles:

3–5 mg of freeze dried microparticles, accurately weighed, were treated with 1.0 ml, 0.1M NaOH containing 5% w/v SDS by shaking overnight on a Ika Vibrax -VXR shaker.

The sample was centrifuged and a BCA protein microassay was used to determine the OVA concentration in the supernatant against a series of OVA standards prepared in 0.1M NaOH containing 5% w/v SDS. Each sample was assayed in duplicate.

Particle Size:

Particles were sized by laser diffractometry using a Malvern 2600D laser sizer. Average particle size was expressed as volume mean diameter (vmd) in $\mu$m.

Span in the microparticle formulation has been found to be effective in reducing the burst effect of surface protein, and influences particle size and protein payload (Table 1). When Span 60 was used as a stabiliser in the primary emulsion, the protein entrapment increased with increasing concentration of surfactant, to a peak value of approximately 16% OVA at 3% Span concentration then decreased with increasing surfactant concentration from 3 to 20%. The mean particle size was between 10 and 20 $\mu$m, and the smallest particles were obtained in the absence of Span 60.

TABLE 1

Investigation of the effect of Span 60 concentration in the primary emulsion.

| Span Conc. %. | Protein Entrapment % | Entrapment Efficiency % | Particle size ($\mu$m) vmd |
|---|---|---|---|
| 0 | 10.7 | 90.2 | 9.3 |
| 0.5 | 10.4 | 89.3 | 12.6 |
| 1.0 | 11.5 | 82.7 | 18.2 |
| 2.0 | 12.2 | 93.5 | 16.3 |
| 3.0 | 15.8 | 98.9 | 16.9 |
| 5.0 | 12.6 | 87.9 | 15.1 |
| 10.0 | 11.3 | 78.8 | 10.9 |

Example 3. The effect of PLG/PEG 8000 solution ratio

A solution of Span 60 (3.0%, 2 ml) in DCM was emulsified with an OVA aqueous solution (1 ml, 30 mg/ml) to -provide the primary emulsion. The resulting w/o emulsion was then emulsified at high speed with polymer solution (6% w/v) consisting of PLG blended with different ratios of PEG 8000 in DCM. The emulsion was then mixed with a continuous phase solution, methanol, containing 10% w/v PVP as an emulsion stabilizer. The resulting w/o/o emulsion was stirred for 3–4 hours under ambient conditions to extract DCM. The microparticles were cleaned, freeze dried and stored as described above.

With 3% Span 60 as a surfactant in the primary emulsion, a clear relationship was found between protein entrapment and PLG/ PEG 8000 solution ratios (Table 2). The 1:3 solution ratio resulted in the highest protein entrapment (72%). The protein entrapment (% w/w) increased with increasing solution ratio from 0 to 1:3 and then decreased with increasing solution ratio from 1:4 to 1:5. The mean particle size varied between 7 and 18 $\mu$m, depending on PLG:PEG solution ratio and the smallest particles (6.6 $\mu$m) were obtained using a polymer solution ratio of 1:1.

TABLE 2

The effect of PLG/PEG 8000 solution blend ratio on microparticle size and protein loading

| PLG/PEG 8000 | Protein Entrapment % | Entrapment Efficiency % | Particle size ($\mu$m) vmd |
|---|---|---|---|
| 1:0 | 16.3 | 94.3 | 18.6 |
| 1:1 | 43.1 | 83.4 | 6.6 |

TABLE 2-continued

The effect of PLG/PEG 8000 solution blend ratio on microparticle size and protein loading

| PLG/PEG 8000 | Protein Entrapment % | Entrapment Efficiency % | Particle size (μm) vmd |
|---|---|---|---|
| 1:2 | 52.8 | 87.5 | 18.9 |
| 1:3 | 72.3 | 89.8 | 14.7 |
| 1:4 | 39.2 | 85.7 | 10.7 |
| 1:5 | 36.8 | 91.5 | 11.1 |

Example 4. The effect of the stabiliser concentration in the continuous phase A solution of Span 60 (0.5%, 2 ml) in DCM was emulsified with an OVA aqueous solution (1 ml, 30 mg/ml) to provide the primary emulsion. The resulting emulsion was then emulsified at high speed with polymer solution (6% w/v 1:5 PLG/ PEG 8000 in DCM) and emulsified with a continuous phase solution, methanol, containing from 5 to 25% w/v PVP as an emulsion stabilizer. The resulting w/o/o emulsion was stirred for 3–4 hours under ambient conditions to extract DCM. The microparticles were cleaned, freeze dried and stored as described above.

The mean particle size varied between 10 and 20 μm (Table 3). Protein loading remained fairly constant between 30 and 36% (Table 1). No significant effects of PVP concentration between 5 and 25% on OVA entrapment are evident.

TABLE 3

The effect of PVP concentration in the continuous phase on microparticles size and protein loading

| PVP % | Protein Entrapment % | Entrapment Efficiency % | Particle size (μm) vmd |
|---|---|---|---|
| 5 | 36.1 | 83.1 | 19.7 |
| 10 | 33.1 | 92.5 | 17.7 |
| 15 | 30.7 | 96.6 | 16.8 |
| 20 | 32.1 | 95.4 | 18.5 |
| 25 | 34.9 | 87.7 | 10.6 |

Example 5. The effect of volume of reagents on microparticle characteristics produced using PLG/PEG solutions The effect on microparticle characteristics of increasing the volume of polymer solution. The volume ratio of OVA/Span/polymer solution/continuous phase (1/2/5/20) was kept constant. A solution of Span 60 (0.5%) in DCM (2, 4 and 8 ml) was emulsified with an aqueous OVA solution 30 mg/ml, (1, 2 and 4 ml). The resulting emulsion was then mixed at high speed with the polymer solution (6% w/v PLG/ PEG 8000: 1/5 in DCM ) (5, 10, 20 ml) and emulsified with a continuous phase solution (20, 40, 80 ml), methanol, containing 15% w/v PVP as an emulsion stabilizer. The resulting w/o/o emulsion was stirred for 3–4 hours under ambient conditions to extract DCM. The microparticles were cleaned, freeze dried and stored as described above.

The effect on microparticle characteristics of increasing the volume of polymer solution (at constant volume ratio of OVA/Span/polymer solution/continuous solution/(1/2/5/20)) is shown in Table 4. The protein entrapment was found to increase with increasing volume from 31.6% w/w to 47.8% w/w and the particle size decreased with increasing volume from 16.7 to 2.1 μm.

TABLE 4

The effect of polymer solution volume on microparticle size and protein loading

| Volume of Polymer solution | Protein Entrapment % | Entrapment Efficiency % | Particle size (μm) vmd |
|---|---|---|---|
| 5 | 31.6 | 94.6 | 16.7 |
| 10 | 39.2 | 96.5 | 8.6 |
| 20 | 47.8 | 98.3 | 2.1 |

Example 6. Protein release microparticles

In-vitro Release of Ovalbumin from Microparticles:

A series of tubes, each containing approximately 20 mg freeze-dried microparticles (accurately weighed) and dispersed in 2.0 ml PBS, were retained in a water-bath at 37° C. with occasional shaking. Periodically, the microparticle samples were centrifuged (3,800 rpm 5 minutes), the supernatant was removed and the protein content of the supernatant was analyzed using a BCA protein assay. Fresh PBS was added to the microparticles and incubation was continued. Release profiles were calculated both in terms of cumulative release (%) with incubation time and μg OVA/mg of microparticles with incubation time.

The protein release characteristics from microparticles produced by the method disclosed herein are shown in FIG. 1. Cumulative release amount (μg/mg) vs. time relationships are shown. It can be seen that the release pattern follows a zero order release profile. The blended PLG/PEG microparticles prepared according to the invention result in at least a four fold increase in protein release compared with PLG microparticles, produced by the standard methods described in the prior act (Wang, et al).

Example 7. Microparticles prepared from blended solutions of lactide polymers and PEG The effect of lactide polymer type on microparticle characteristics OVA-loaded microparticles were prepared according to the method described in Example 3 but using polymers of different lactide:glycolide ratio in a 1:2 blend with PEG. The microparticle characteristics are shown in Table 5. The maximum protein loading level of around 40% was achieved using poly(D,L-lactide) polymer with PEG 8000. The smallest particle size was obtained using 75:25 PLG. Thus it can be seen that the use of different biodegradable polymers in the microparticles formulations as the slow resorbing phase can allow variation of protein loading and microparticle size.

TABLE 5

Investigation of the effect of lactide polymer type on particle characteristics

| PLG Type* | Protein Entrapment % | Entrapment Efficiency % | Particle size (μm) | | |
|---|---|---|---|---|---|
| | | | vmd | d(90) | d(10) |
| 50:50 | 26.6 | 95.6 | 10.6 | 19.4 | 2.8 |
| 75:25 | 21.8 | 81.3 | 7.7 | 12.9 | 2.4 |
| 85:15 | 28.1 | 99.8 | 11.8 | 28.0 | 1.8 |
| 100:0 | 40.3 | 95.2 | 13.6 | 33.8 | 2.4 |

*: lactide/glycolide ratio.

Average volume mean diameter (vmd); Particle diameter d(90): 90% below this range; Particle diameter d(10): 10% below this range.

Example 8. The Effect of PLG:Pluronic 127 Solution Composition on Microparticle Characteristics A solution of Span 60 (2 ml, 0.5% w/v) in DCM was emulsified with an OVA aqueous solution (1 ml, 30 mg/ml) using a Silverson homogeniser to produce a primary emulsion. The resulting emulsion was then mixed at high speed with a 6% (w/v) polymer solution produced by co-dissolving PLG and Pluronic F127 in DCM in various ratios: 3:1, 1:1, 1:2 and 1:3. The resulting w/o emulsion was mixed with a continuous phase solution methanol containing 15 % w/v PVP as an emulsion stabilizer and the resulting w/o/o emulsion was stirred with a magnetic stirrer for 3–4 hours under ambient conditions to extract DCM. The microparticles were cleaned, freeze dried and stored as described in Example 1.

Samples are designated in the text in terms of the ratio of PLG to Pluronic in the starting polymer solution.

The effect of PLG:Pluronic F127 solution composition on microparticle characteristics is shown in Table 6. Blending of Pluronic F127 with PLG results in an improvement of protein loading relative to PLG microparticles. The maximum loading level achieved of around 30% (1:2 PLG:Pluronic F127) is almost twice that obtained with PLG (16%) in similar size microparticles. No distinct relationship between protein entrapment and PLG:Pluronic F127 ratio is apparent (Table 6). The microparticle size is seen to decrease with increasing Pluronic F127 ratio in the starting solution from 17.4 $\mu$m (3:1) to 6.4 $\mu$m (1:3). PLG:Pluronic F127 ratios above 1:3 did not result in microparticle formation.

TABLE 6

The effect of PLG:Pluronic F127 solution composition on microparticle characteristics

| PLG Pluronic ratio | Protein Entrapment % | Entrapment Efficiency % | Particle size ($\mu$m) | | |
|---|---|---|---|---|---|
| | | | vmd | d(90) | d(10) |
| 1:0 | 16.3 | 94.3 | 18.6 | 45.7 | 2.1 |
| 3:1 | 22.4 | 99.5 | 17.7 | 42.7 | 1.9 |
| | 21.8 | 99.8 | 17.0 | 40.7 | 1.9 |
| 1:1 | 17.5 | 100 | 11.9 | 26.8 | 2.0 |
| | 18.3 | 99.9 | 11.9 | 25.8 | 2.2 |
| 1:2 | 29.7 | 99.1 | 9.51 | 25.8 | 1.9 |
| | 28.9 | 98.9 | 9.45 | 24.3 | 2.0 |
| 1:3 | 27.8 | 96.1 | 6.4 | 14.8 | 1.5 |
| | 28.5 | 95.7 | 6.4 | 15.0 | 1.6 |

Average volume mean diameter (vmd); Particle diameter d(90): 90% below this range; Particle diameter d(10): 10% below this range. Results tabulated correspond to 2 separate batches of microparticles.

Example 9. The Effect of Reagent Volume on Microparticle Characteristics
(PLGPluronic blend solution)

The volume ratio of OVA/Span/polymer solution/ continuous phase solution (1/2/5/20) was kept constant. An OVA aqueous solution (1, 2 or 4 ml) was emulsified with a solution of Span 60 (0.5% (w/v)) in DCM (2, 4 or 8 ml, respectively). The resulting emulsion was then mixed at high speed with polymer solution (6% w/v, 1:1 PLG : Pluronic F127 in DCM) (5, 10 or 20 ml) and emulsified with a continuous phase solution (20,40 or 80 ml), methanol, containing 15% w/v PVP as an emulsion stabilizer. The resulting w/o/o emulsion was stirred for 3–4 hours under ambient conditions to extract DCM. The microparticles were cleaned, freeze dried and stored as described in Example 1.

Protein entrapment was found to be unaffected by increasing the volume of reagents at constant volume ratio (Table 7). The microparticle size tends to decrease with an increase in reagent volume and the particle size distribution is improved.

The small 3–4 $\mu$m microparticles produced by increasing the volume of reagents are potentially suitable for intravenous administration and oral vaccine formulations. In the latter case, microparticles interaction with the Peyer's patches of gut associated lymphoid tissue is enhanced if the particle size is less than 5 $\mu$m.

TABLE 7

The effect of reagent volume on microparticle characteristics (1:1 PLG:Pluronic F127)

| Polymer solution volume | Protein Entrapment % | Entrapment Efficiency % | Particle size ($\mu$m) | | |
|---|---|---|---|---|---|
| | | | vmd | d(90) | d(10) |
| 5 | 17.4 | 97.2 | 7.9 | 12.6 | 1.6 |
| | 16.9 | 96.5 | 8.0 | 13.1 | 1.7 |
| 10 | 18.1 | 98.0 | 3.9 | 6.9 | 1.4 |
| | 18.3 | 100 | 3.4 | 6.0 | 1.4 |
| 20 | 15.9 | 75.4 | 4.0 | 7.1 | 1.5 |
| | 16.4 | 76.8 | 4.1 | 7.4 | 1.5 |

Average volume mean diameter (vmd); Particle diameter d(90): 90% below this range; Particle diameter d(10): 10% below this range. Results tabulated correspond to 2 separate batches of microparticles.

Example 10. Microparticles prepared from blended solutions of lactide polymers and Pluronic The effect of lactide polymer type on microparticle characteristics OVA-oaded microparticles were prepared according to the method described in Example 8 but using polymers of different lactide:glycolide ratios in a 1:1 blend with Pluronic F127.

The maximum loading level of approximately 40% OVA was found to be obtained using 75:25 PLG copolymer (Table 8). The microparticle size was found to increase with increasing lactide content of the copolymer. The use of poly(D,L-lactide) did not result in microparticle formation.

TABLE 8

The effect of lactide polymer type on microparticle characteristics (1:1 PLG:Pluronic F127 solution).

| PLG Type* | Protein Entrapment % | Entrapment Efficiency % | Particle size ($\mu$m) | | |
|---|---|---|---|---|---|
| | | | vmd | d(90) | d(10) |
| 50:50 | 14.1 | 70.6 | 7.8 | 17.4 | 1.8 |
| 75:25 | 40.5 | 52.2 | 10.1 | 22.4 | 2.3 |
| 85:15 | 16.3 | 80.3 | 19.6 | 38.5 | 3.0 |
| 100:0 | no microparticles formed | | | | |

*: lactide/glycolide ratio.

Average volume mean diameter (vmd); Particle diameter d(90): 90% below this range; Particle diameter d(10): 10% below this range.

Example 11. Microparticles prepared from blended solutions of PLG and Pluronic The effect of Pluronic Type on microparticle characteristics The adjuvant effect of Pluronic PEO-PPO copolymers such as Pluronic L121 has been reported by several groups of workers (Hunter. et al). Several other preparations using PEO-PPO copolymers with shorter PPO or longer hydrophilic PEO chains also demonstrated adjuvant activity. Thus microparticulate vaccines prepared from blends of PLG and Pluronic may result in improved adjuvanticity.

OVA-loaded microparticles were prepared according to the method described in example 8 but using different types of Pluronic PEO-PPO copolymers in a 1:2 blend solution with PLG and decreasing the polymer solution concentration to 3%.

The effect of Pluronic type on microparticle characteristics is shown in Table 9. An OVA loading level of around 40% in similar size microparticles 3.9–6.2 μm was routinely achieved. No distinct relationship between micropartide size and Pluronic types was apparent (Table 9). The high OVA loading may result partly from the use of a lower polymer solution content (ie 3% rather than 6%).

TABLE 9

The effect of Pluronic type on microparticle characteristics (1:2 PLG:Pluronic solution)

| Pluronic Type | OVA Entrapment % | Entrapment Efficiency % | Particle size (μm) | | |
|---|---|---|---|---|---|
| | | | vmd | d(90) | d(10) |
| L44 | 44.2 | 100 | 6.2 | 11.9 | 1.2 |
| L121 | 40.3 | 100 | 4.5 | 8.6 | 1.3 |
| L122 | 42.9 | 100 | 4.8 | 9.3 | 1.4 |
| L123 | 41.2 | 100 | 3.9 | 7.3 | 1.2 |
| F127 | 45.9 | 100 | 4.8 | 9.45 | 1.4 |

Average volume mean diameter (vmd); Particle diameter d(90): 90% below this range; Particle diameter d(l0): 10% below this range.

Example 12. OVA release from microparticles prepared from PLG:Pluronic blended solutions The cumulative release of OVA from various microparticle formulations is plotted vs time in FIGS. 3 and 4. The change in release pattern and release amount obtained by blending PLG with Pluronic F127 in solution to produce the carrier matrix is apparent. The cumulative release amounts for 1:2 and 1:3 PLG:Pluronic microparticles after one month incubation in PBS at 37° C. are similar, amounting to 100 μg OVA/mg microparticles and 110 μg OVA/mg microparticles respectively. The results of curve fitting programmes (PCNONLIN) suggest that protein release from the 1:2 PLG:Pluronic and 1:3 PLG:Pluronic systems conforms to the Higuchi model (release amount dependence on the square root of time). The diffusion rate constants (D) are respectively 19.8 and 20.4 (μg/mg.day$^{0.5}$).

In the case of 3:1 and 1:1 PLG:Pluronic microparticles, the protein release pattern is similar and appears to be following a linear, zero order release profile with a release rate constant ($k_o$) of 1.3 and 0.97 (μg/mg.day), respectively.

The rapid and efficient protein delivery which characterises the PLG:Pluronic microparticles is expected to be facilitated by Pluronic modified internal surfaces within the carrier which would modulate protein/polymer interactions. The properties of the microparticle matrix such as the propensity for porosity development and the pattern of drug release are expected to be controllable by adjusting the amount and the molecular characteristics of the Pluronic copolymer incorporated in the starting solution. The protein release rate and cumulative amount released is expected to increase with increasing amounts of hydrophilic Pluronic copolymers in the blend and with decreasing molecular weight of the Pluronic copolymers.

Example 13. Insulin-loaded microparticles

Preparation

A solution of Span 60 (2 ml, 0.5% w/v) in DCM was emulsified with an aqueous insulin solution (1 ml, 50 mg/ml) to provide a primary emulsion. The resulting emulsion was then mixed at high speed with a 5 ml of 6% (w/v) polymer solution produced by co-dissolving PLG and PEG 8000 in DCM in a ratio: 1:2. The resulting w/o emulsion was mixed with 20 ml of continuous phase solution, methanol, containing 10% w/v PVP as an emulsion stabilizer. The resulting w/o/o emulsion was stirred with a magnetic stirrer for 3–4 hours under ambient conditions to extract DCM. The microparticles were cleaned by centrifuging and resuspension in distilled water a total of three times and then freeze dried. The final product was stored in a desiccator below 4° C.

Determination of insulin loading of microparticles by HPLC

Assay procedure: The chromatographic system consisted of a Lichrospher 100 RP-18 5 μm particle diameter (Merck) (0.46×15 cm) column, a LKB 2150 HPLC solvent delivery pump, a Gilson dilutor model 401 sample injector and a LKB 2152 HPLC controller. Peak detection was by UV absorbency at 220 nm using a LKB 2151 variable wavelength detector. Quantification (by peak area) and recording of chromatograms was accomplished using a HP 3394A integrator.

The mobile phase consisted of acetonitrile:water 32:68, with 0.06% TFA, which was degassed with helium prior to use. A flow rate of 2.0 ml/min was utilised at room temperature, which resulted in a retention time for the insulin peak of 6 minutes. The sample injection volume was set at 50 μl and samples were assayed in triplicate. The minimum detectable concentration of insulin was 1 μg/ml, and the regression relationship for the calibration curve of insulin peak area vs. concentration (between 1 and 100 μg/ml) was over 0.997.

Extraction of insulin from microspheres:

Insulin was extracted from the microparticles by the following process. 10 mg of insulin-loaded microparticles were dissolved in 1 ml of NN-dimethylacetamide: 1, methyl-2-pyrrolidinone (1:1 ratio) and added to 1.0 ml of acetonitrile. The mixture was agitated using a mechanical shaker for 3 min. 2 ml of 0.1N phosphate buffer solution (pH 7.4) were added and the tube contents were centrifuged at 3500 rpm for 10 min. The supernatant was centrifuged again at 13600 rpm for 5 min, then 50 μl of this solution was analyzed by HPLC. Each sample was assayed in triplicate and the insulin concentration was determined by comparison with a calibration curve.

In-vitro release of insulin from microparticles:

A series of tubes, each containing approximately 20 mg freeze-dried microparticles, accurately weighed. were dispersed in 2.0 ml PBS containing 0.01% of methyl cellulose, and retained in a water-bath at 37° C. with occasional shaking. Periodically, the microparticle samples were centrifuged (3,600 rpm 5 minutes), and the supernatant was collected and recentrifuged at 13600 rpm for 5 min. 50 μl of this solution was injected onto the HPLC column. Fresh PBS was added to the microparticles and incubation was continued. Release profiles were calculated both in term of cumulative release (% w/w) with incubation time and cumulative release (μg insulin/mg microparticle) with incubation time.

The initial insulin content of microparticles, and the insulin content of microparticles after washing in PBS solution at room temperature for 4 hours to remove surface insulin are shown in Table 10. The initial insulin loading level was approximately 17% w/w, which was reduced after washing to a loading level of approximately 5%. Thus a large proportion of the insulin originally associated with the microparticles is surface located.

Figure 3:
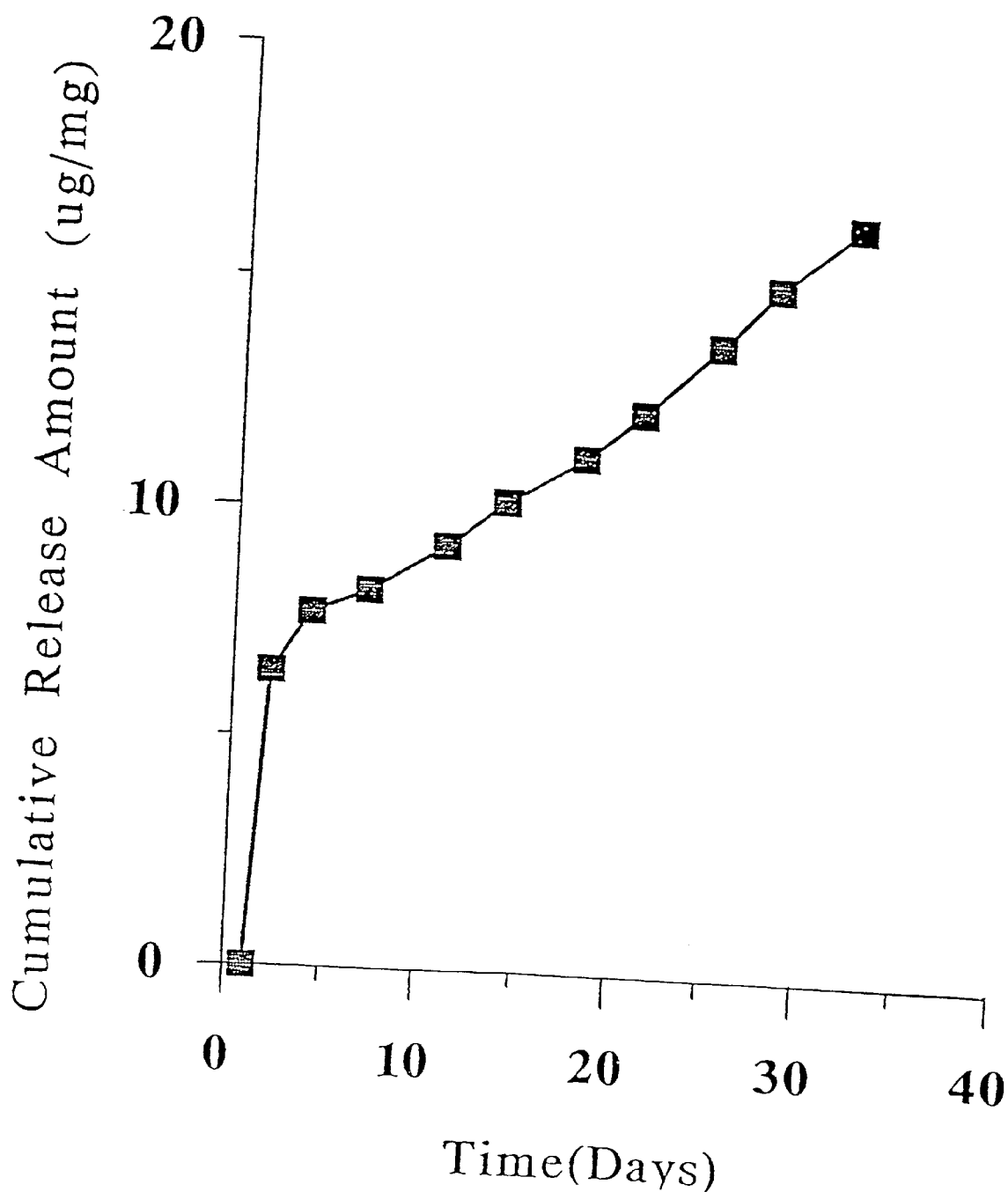
FIG. 3 is a graph showing the cumulative release profiles of insulin from PLG microparticles prepared using PLG:PEG solution.

The cumulative release amount of insulin from washed microparticles after one month incubation in PBS at 37° C. was approximately 30 µg insulin/mg microparticles (FIG. 3). A significant 'burst effect' of surface located insulin occurred from washed microparticles in the first 3 days of release testing amounting to approximately 47% of the insulin content. After 3 days, uniform release of insulin occurred with a release rate of 0.6 µg/mg/day.

TABLE 10

The insulin content (w/w %) of microparticles prepared from 1:2 PLG:PEG blend solution.

| Initial Insulin Loading (w/w %) | Retained Insulin Content (w/w %) after washing in PBS |
|---|---|
| 16.8 | 5.1 |
| 16.9 | 4.9 |

Attempts have been made in the prior art to entrap insulin in microparticles. Kwong et al. described the preparation of insulin loaded poly lactic acid particles that were over 100 µm in size. A burst release effect occurred during the first hour at 0° C. of more than 50% of the insulin load. Slow release of the remaining insulin was the obtained. The duration of action of the particles could be varied from a few hours to several days. The insulin content of these particles described in the prior art was less than 5% w/w before washing. This value dropped to 2% w/w or less after washing.

Example 14. LHRH-loaded microparticles

Preparation

A solution of Span 60 (2 ml, 0.5% w/v) in DCM was emulsified with an aqueous LHRH solution (1 ml, 50 mg/ml) to provide a primary emulsion. The resulting emulsion was then mixed at high speed with a 5 ml of 6% (w/v) polymer solution produced by co-dissolving PLG and PEG 8000 in DCM in a ratio of 1:2. The resulting w/o emulsion was mixed with 20 ml of continuous phase solution, methanol, containing 10% w/v PVP as an emulsion stabilizer. The resulting w/o/o emulsion was stirred with a magnetic stirrer for 3–4 hours under ambient conditions to extract DCM. The microparticles were cleaned by centrifuging and resuspension in distilled water a total of three times and then freeze dried. The final product was stored in a desiccator below 4° C.

The assay procedure used for determination of LHRH loading of microparticle is as described in Example 13.

The LHRH content of microparticles, and the corresponding microparticle size range are shown in Table 11.

TABLE 11

The LHRH content (w/w %) and particle size of microparticles prepared from 1:2 PLG:PEG blend solution.

| Application | Protein Entrapment % | Particle size range (µm) |
|---|---|---|
| LHRH | 27.9 | 5–10 |

Example 15. DNA-loaded microparticles

A solution of Span 60 in DCM (2 ml, 0.5% w/v) was emulsified with 1 ml of a DNA aqueous solution (1 mg Plasmid PT 7T3, 400 µl water, 200 µl ethanol, 400 µl TE (Tris/EDTA) pH 8.5). The emulsion was mixed for 2 minutes with 5 ml of polymer solution in DCM (6% w/v, 1:1 PLG:PEG) and emulsified for 4 minutes with a continuous phase solution, methanol (20 ml) containing 10% w/v PVP as an emulsion stabiliser. The resulting W/O/O emulsion was stirred for 3–4 hours under ambient conditions to extract DCM. The microparticles were cleaned by centrifuging and resuspension in distilled water, then freeze dried and stored in a dessicator below 4° C.

Examination of the microparticles using scanning electron microscopy revealed two populations of roughly spherical microparticles, one having diameters ranging from 10 to 40 µm, the second having a mean diameter of approximately 100 µm.

Microparticles were treated with chloroform/water to extract DNA and the DNA was detected by agarose gel electrophoresis. The presence of a band on the gel was revealed by a UV transilluminator confirming the presence of DNA in the microparticle sample.

REFERENCES

1. Florence, et al., Controlled release of drug polymers and aggregate systems, Morton Rosoff, VCH publishers, N.Y., 1988, 163–184.
2. Watts, et al., Crit. Rev. Ther. Drug Carrier Syst., 7, (1990) 235–259.
3. Cohen, et al., Pharm. Res., 8, (1991) 713–720.
4. Wang, et al., J. Cont. Rel, 17, (1991) 23–32.
5. Fong, et al., J. Cont. Rel, 3, (1986) 119–130.
6. Bodmeier, et al, Pharm. Res., 4, (1987) 465–471.
7. Benita, et al., J. Pharm. Sci., 73, (1984) 1721–1725.
8. Alonso, et al., Pharm. Res., 10, (1993) 945–953.
9. Leelarasamee, et al., J. Microencapsulation, 5, (1988) 147–157.
10. Wada, et al., Pharm. Res., 8, (1991) 1292–1296.
11. Ogawa, et al., Chem. Pharm. Bull., 36, (1988) 1095–1103.
12. Jeffery, et al., Int. J. Pharm., 77, (1991)169–175.
13. Jeffery, et al., Pharm. Res., 10, (1993) 362–368.
14. Singh, et al., Pharm. Res., 8, (1991) 958–961.
15. Singh, et al., Int. J. Pharm., 85, (1992) R5–R8.
16. Raghuvanshi, et al., Int. J. Pharm., 93, (1993) R1–R5.
17. Visscher, et al., J. Biomedical Material Res., 22, (1988) 733–746.
18. Eldridge, et al., Infer. Immun., 59, (1991) 2978–2983.
19. Eldridge, et al., Curr. Top. Micro. Immunol., 146, (1989) 59–66.
20. Jenkins, et al., Int. J. Pharm, 102, (1994) 261–266.
21. Jani, et al. J. Pharm. Pharmacol., 41, (1989) 809–812.
22. Eldridge, et al., J. Cont. Rel., 11, (1990) 205–209.
23. Hora, et al., Pharm. Res., 7, (1990) 1190–1194.
24. Smith, et al., Anal. Biochem., 150, (1985) 76–82.
25. Fessi, et al., Demande de Brevet D'invention, Republique Francaise, No. 2608988,1986.
26. Kwong et al., J. Control. Release 4, (1986) 47–62
27. Hunter, et al., Vaccine, 9 (1991) 250–256.

We claim:

1. A microparticle comprising a mixture of:
   (a) a biodegradable polymer,
   (b) a water soluble polymer which has a molecular weight of about 8000 Daltons or higher, and (c) an active agent;
characterised in that the microparticle exhibits an active agent release profile which is substantially linear with time.

2. A microparticle comprising a mixture of:
   (a) a biodegradable polymer,
   (b) a water soluble polymer, and
   (c) an active agent;
wherein the water soluble polymer is a block copolymer comprising PEG as one of the blocks.

3. The microparticle of claim 1 wherein the water soluble polymer is a block copolymer comprising PEG as one of the blocks.

4. The microparticle of claim 1 wherein the microparticle has a size in the range of between about 10 nm and 200 μm.

5. The microparticle of claim 1 wherein the biodegradable polymer is a lactide homopolymer or a copolymer of lactide and glycolide.

6. The microparticle of claim 5 wherein the biodegradable polymer is poly(lactide co-glycolide) with a molecular weight in the range of between about 5 and 100 kD.

7. The microparticle of claim 1 wherein the active agent is a peptide, polypeptide or a protein.

8. The microparticle of claim 1 wherein the active agent is selected from the group consisting of DNA, vaccines, allergens and antigens.

9. The microparticle of claim 8 wherein the active agent is selected from the group consisting of insulin, luteinizing hormone releasing hormones, growth hormones, interferons colony stimulating factors, and somatostatin.

10. The microparticle of claim 1 wherein the ratio of the biodegradable polymer to the water soluble polymer is in the range of between about 99.9:1.0 and 10:90.

11. The microparticle of claim 1 which is suitable for administration by intramuscular, intravenous, subcutaneous, intraarticular or intraperitoneal injection.

12. The microparticle of claim 1 which is suitable for administration to the dermal or epidermal layer of the skin by injection or needleless injector system.

13. The microparticle of claim 1 which is suitable for administration to the eye, nose, oral cavity, gastrointestinal tract or vaginal cavity.

14. The microparticle of claim 1 which is suitable for administration to plants.

15. A method of forming polymer microparticles containing an active agent comprising the steps of:

a. forming an aqueous solution, water-in-oil (W/O) emulsion or a suspension of the active agent in a first organic solvent;
   b. mixing the aqueous solution, W/O emulsion or suspension of the active agent with a polymer solution formed in a second organic solvent; and
   c. mixing the emulsion so formed in step b. with a continuous phase comprising a third organic solvent which is miscible with the first and second organic solvents and is not a solvent for the polymer.

16. The method of claim 15 wherein the solvent used to produce the water-in-oil emulsion or the suspension of the active agent contains the dissolved polymer and step b. is omitted.

17. The method of claim 15 wherein the polymer solution comprises a mixture of a biodegradable polymer and a water soluble polymer.

18. The method of claim 15 wherein the third organic solvent is a lower alcohol between one and six carbon atoms.

19. The method of claim 18 wherein the third organic solvent is methanol.

20. The method of claim 15 wherein the first and second organic solvent are the same or different and are selected from dichloromethane (DCM), chloroform, acetone, ethyl acetate, ethyl formate and miscible mixtures thereof.

21. The method of claim 15 wherein the first organic solvent contains a stabiliser.

22. The method of claim 15 wherein the continuous phase contains a surfactant.

23. A method of administering an active agent to an animal or human comprising administering a microparticle comprising a mixture of
   (a) a biodegradable polymer,
   (b) a water soluble polymer, and
   (c) the active agent,
wherein the microparticle exhibits an active agent release profile which is substantially linear with time.

24. A microparticle obtained by the method of claim 15.

25. The microparticle of claim 24 wherein the microparticle exhibits an active agent release profile which is substantially linear with time.

26. The microparticle of claim 24 wherein the water soluble polymer is a block copolymer comprising PEG as one of the blocks.

* * * * *